United States Patent
Adamoli, Jr. et al.

(10) Patent No.: US 7,357,946 B2
(45) Date of Patent: Apr. 15, 2008

(54) USES FOR CELLULOSE-CONTAINING AGGREGATES

(76) Inventors: James R. Adamoli, Jr., 1326 Country Place Cir., Houston, TX (US) 77079; Mark A. Adamoli, 5915 Havenwoods Dr., Houston, TX (US) 77066

( * ) Notice: Subject to any disclaimer, the term of this patent is extended or adjusted under 35 U.S.C. 154(b) by 706 days.

(21) Appl. No.: 10/619,705

(22) Filed: Jul. 15, 2003

(65) Prior Publication Data

US 2004/0033901 A1  Feb. 19, 2004

Related U.S. Application Data

(60) Continuation-in-part of application No. 09/867,073, filed on May 29, 2001, now Pat. No. 6,593,277, which is a division of application No. 09/395,470, filed on Sep. 14, 1999, now abandoned, which is a continuation-in-part of application No. 08/880,901, filed on Jun. 23, 1997, now Pat. No. 5,951,995, which is a continuation-in-part of application No. 08/479,171, filed on Jun. 7, 1995, now abandoned, which is a continuation-in-part of application No. 08/228,443, filed on Apr. 15, 1994, now abandoned.

(51) Int. Cl.
*A61K 47/38* (2006.01)

(52) U.S. Cl. .................... 424/474; 47/56; 47/57.6; 71/64.13; 111/916; 424/400; 424/488; 514/781

(58) Field of Classification Search .................... None
See application file for complete search history.

(56) References Cited

U.S. PATENT DOCUMENTS

| | | |
|---|---|---|
| 351,897 A | 11/1886 | Boyer |
| 4,504,468 A | 3/1985 | Brill et al. |
| 5,154,594 A | 10/1992 | Gamlen |
| 5,320,066 A | 6/1994 | Gunter |
| 5,674,806 A | 10/1997 | Adamoli, Jr. et al. |
| 5,885,600 A | 3/1999 | Blum et al. |
| 5,951,995 A | 9/1999 | Adamoli, Jr. et al. |
| 6,009,663 A * | 1/2000 | Kazemzadeh ............... 47/57.6 |
| 6,325,969 B1 | 12/2001 | Aamodt et al. |
| 6,523,299 B2 * | 2/2003 | Morris ............................ 47/9 |
| 6,593,277 B2 | 7/2003 | Adamoli, Jr. et al. |

* cited by examiner

*Primary Examiner*—Neil S. Levy
(74) *Attorney, Agent, or Firm*—John R Casperson

(57) ABSTRACT

Aggregates of cellulose-containing particles, such as particles of waste paper and optional other vegetation or waste particles are used as a carrier for additives such as insecticides, herbicides, fertilizers and nutrients. The particles can be also used as a carrier for insect repellants, preferably naturally occurring insect repellants, to repel insects from rooms, buildings, plants, and outdoor areas, and to carry adhered seeds onto an area to be planted with seeds.

4 Claims, No Drawings

USES FOR CELLULOSE-CONTAINING AGGREGATES

This application is a continuation in part of application Ser. No. 09/867,073, filed May 29, 2001, now U.S. Pat. No. 6,593,277, which was a division of then application Ser. No. 09/395,470, filed Sep. 14, 1999, now abandoned, which was a continuation-in-part of then application Ser. No. 08/880,901, filed Jun. 23, 1997, now U.S. Pat. No. 5,951,995 issued Sep. 14, 1999, which was a continuation-in-part of then application Ser. No. 08/479,171, filed Jun. 7, 1995, now abandoned, which was a continuation-in-part of then application Ser. No. 08/228,443, filed Apr. 15, 1994, now abandoned.

BACKGROUND OF THE INVENTION

This invention relates to the use of cellulose products such as recycled paper.

Waste products such as waste paper, lawn clippings, wood chips, gin trash, banana peels, shrubbery, sugar cane, sorghum, other vegetation and plastics are filling landfills. Alternatives to current disposal of these products would be very desirable.

Certain insects, such as termites and fire ants, are difficult to control and cause much damage. Improved techniques for controlling these insects would be very desirable. A technique for better controlling these insects which makes use of the above described waste products would be especially desirable.

Herbicides are used throughout the country to control the growth of unwanted plants. More effective techniques for applying herbicides would reduce the amount of herbicide being released into the environment and would be very desirable. A more effective technique which makes use of the above waste materials would be even more desirable.

Denuded landscape is a common byproduct of agricultural and construction activities. For steeply pitched land, especially, the lack of ground cover can lead to loss of surface and topsoil due to water erosion. A technique to promote revegetation would be very desirable. A revegetation technique which makes use of the above waste materials would be even more desirable.

OBJECTS OF THE INVENTION

It is an object of this invention to provide cellulose-containing products, especially products formed from waste paper such as newsprint, in a form so that it is highly suitable for horticultural and agricultural uses, and for insect control.

SUMMARY OF THE INVENTION

In one embodiment of the invention, the aggregates of cellulose particles can be employed in a method for controlling plant growth. The method is carried out by selecting an area in which plant growth control is desired and applying aggregates of cellulose-containing particles containing a plant growth inhibitor to the area. Generally, the type of plant growth desired to be inhibited will be weed growth or grass growth. The area to be treated will generally comprise a horticultural area In such case, the plant growth inhibitor will generally comprise a herbicide. To provide this utility, in one aspect the invention comprises a pellet consisting primarily of ground-up paper which has been impregnated with a plant growth toxin selected from the group consisting of Oryzalin, Isoxaben, Trifluralin, Prodamine, Oxyflurofen+ Pendimethalin, Oxadiazon, Pendimethalin, Benefrin+ Oryzalin, Oxyfurofen+Oxidanzon and Metolachlor in an amount in the range of from about 0.1 to about 10 weight percent.

In another embodiment of the invention, there is provided a method for repelling insects. The method is carried out by selecting an area from which it is desired to repel insects and placing aggregates of cellulose-containing particles containing an insect repellant in the area. The insect repellent is preferably selected from the group consisting of citrus oil, cedar oil, liquid garlic, cloves, citronella oil, white pepper, borax, and boric acid. To carry out this embodiment of the invention, there is provided a pellet consisting primarily of ground-up paper which has been impregnated with an insect repellant selected from the group consisting of citrus oil, cedar oil, liquid garlic, cloves, citronella oil, white pepper, catnip oil, soybean oil, rosemary oil, pennyroyal oil, borax, boric acid and DEET (N,N-diethyl-meta-toluaride) in an amount in the range of from about 0.1 to about 15 weight percent.

In another embodiment of the invention, there is provided a method for seeding an area. The method is carried out by broadcasting pellets or briquettes which contain seed over the area. The pellets or briquettes comprise a core of primarily ground up paper and an adhesive coating over the core carrying the seeds.

DETAILED DESCRIPTION OF THE PREFERRED EMBODIMENTS

The cellulose containing particles are generally of paper and/or vegetable matter origin. When paper is present in the aggregates, it can be present over a wide range. For example, the paper can be present in an amount to provide the aggregate with a paper content in the range of from about 1% to about 99% by weight. Any paper can be used, but the invention will probably have its greatest benefit when applied to recycled paper, including newspapers, telephone books, magazines, computer paper, corrugated paper, etc. Waste or excess paper or pulp recovered from manufacturing processes can also be used. The selection of the desired paper is an economic one, rather than a technical one. Vegetable matter which can be employed as cellulose-containing particles includes wastes from the timber and wood products industry, such as wood, wood chips, lumber and sawdust, wastes from landscaping work such as brush, branches, grass clippings, leaves, and other yard wastes, wastes from agricultural operations such as straw, stalks and leaves; wastes from the processing of agricultural products, such as gin trash, bagasse, grain hulls, peels, sorghum, sugar cane, animal byproducts, food industry sludge, paper industry sludge, clothing industry wastes, or consumer wastes such as discarded clothing and furniture.

Generally speaking, the particles will be of relatively small size. For example, it is expected that utilizing particles which have a maximum size in the range of 1 mm to about 20 mm for a major portion, on a weight basis, of the particles in the aggregates will provide a good result. To provide the particles with this size, it is generally necessary to grind up the starting material. Generally, the paper or other material to be utilized is ground to a screen size of 10 cm or less, usually, to screen size of 3 cm or less, and preferably to a screen size of between about 0.2 and about 2 cm. Hammer mills can be used.

By aggregate is meant a cluster of cellulose-containing particles. Generally speaking, the aggregates are formed from consolidated particles. Preferably, the aggregate is consolidated by compacting ground paper and/or vegetable matter particles under conditions of added moisture, for example by pelletizing or briquetting, to form pellets or briquettes of cellulose-containing particles. For certain applications, however, the aggregate may be in the form of crumb or broken cake. For these applications, broken up pellets or briquette form a highly suitable material. In a case of sprayable insulation or ground cover, the particles are aggregated or consolidated into a mass by spraying them onto the desired surface along with an optional binder and permitting them to dry.

The particle size and shape of the individual aggregates depends on the desired application. Generally speaking, larger aggregate sizes and highly consolidated aggregates will release their added ingredients over a longer period of time than smaller sized or loosely consolidated aggregates. Aggregates which are exposed to the weather, such as on a highway right of way, will lose their added ingredients more quickly than aggregates which are sheltered, such as in an attic or under a foundation.

Generally speaking, the particle size, as expressed in terms of average volume of a major portion of the aggregates, can range from about 0.01 cc to about 1200 cc. Usually, the aggregates will have a volume in the range of from about 0.1 cc to about 800 cc. Preferably, the aggregates will have a volume in the range of from about 0.5 cc to about 150 cc, because it is believed that aggregates having a volume in this range will be useful for most applications. However, for some applications, such as for mulch or ground cover, it may be desirable to form mixtures of aggregates with a volume in the range of 0.5 cc to 150 cc with smaller aggregates which may be in crushed or crumbled form such as those having a size in the range of from about 0.02 cc to about 0.5 cc., although even smaller aggregates such as those having a volume as small as 0.005 cc may also be used.

The aggregates can also be described as having a major dimension and a minor dimension. The minor dimension is preferably less than 5 cm to aid in breakdown and release of the additives. The major dimension is preferably less than about 30 cm to aid in mixing in the soil with standard agricultural implements. The minor dimension is preferably greater than about 0.15 cm and the major dimension is preferably greater than about 0.3 cm for reasons of economy in production and handling. Generally speaking, the aggregates are produced in pellet or briquette form, and can have any desired configuration, such as circular, square, or flattened cross section. The currently preferred aggregate is presently an elongated extrudate with a circular cross-section, because it has been tested with good results. The presently preferred aggregate is generally arcuately shaped and has a length in the range of about 0.1 to about 30 cm and a diameter in the range of from about 0.1 to about 5 cm. Even more preferably, the extrudate has a length in the range of from about 1 to about 15 cm and a diameter in the range of from about 0.2 to about 1.0 cm. An extrudate having a length closely encompassed by the range of from about 2 to about 5 cm and a diameter in the range of from about 0.3 to about 0.8 cm and crumb formed from such an extrudate has been tested in several applications with good results.

The aggregates will generally have an apparent bulk density in the range of from about 110 kg/m$^3$ to about 550 kg/m$^3$ at a moisture level in the range of from about 4-20% by weight.

The formation of pellets of ground paper is known, but not commonly used in the paper recycling industry. A pelletizing machine which extrudes pellets in the form of an extrudate has been used with good results. It is also believed that a briquetting machine, such as is used for the manufacture of charcoal briquettes, would also be useful, as well as equipment for pelletizing animal feeds.

To form the aggregates, the selected cellulose-containing material or mixture thereof is first ground to a particle size suitable for pellet or briquette formation. Generally, the material is ground to a screen size of 10 cm or less, usually, to a screen size of 3 cm or less, and preferably to a screen size of between about 0.2 and about 2 cm. Hammer mills can be used. The aggregates thus contains discrete particles of cellulose waste material in comminuted form. The material is then pelletized or briquetted, or in the case of sprayable materials, generally further ground to a screen size of less than about 2 mm. If necessary, moisture is added in an amount sufficient to facilitate the completion of pellet or briquette formation. Small sized aggregates can be formed, if desired, by crumbling the pellets or briquettes. The aqueous medium may contain a binding agent to facilitate pelletizing. Binding agents include paper products, clay, ash, polymer, or starch-based adhesives, for example. For non-paper cellulose products, the binding agent can comprise paper prepared as hereinabove described.

The aqueous medium can be selected from a wide range of sources. Water is generally suitable. For agricultural and horticultural uses, where the objective is not weed suppression, other aqueous mediums containing organic matter are also suitable. Sewer sludges, paper pulp sludges, sludges containing animal wastes such as chicken litter and/or cattle manure, and slaughterhouse wastes are all suitable. If desired, a growth promoter such as a source of assimilable nitrogen, for example, which is sufficient to provide the pellet product with a ratio of nitrogen to biodegradable carbon in the range of from about 1:10 to about 1:60, on an atomic basis (elemental weight) basis can be incorporated into the product during the pelletizing process. Ammonium nitrate or other commercial fertilizer or chicken litter are suitable.

In another embodiment of the invention, there is provided a method for controlling termite infestation employing the aggregates as described above. In accordance with the method, an area to be protected from the termite infestation is selected and aggregates of cellulose-containing particles containing at least one anti-termite agent are applied around the area to be protected.

The duration of anti-termite agent effectiveness is greatly increased over current methods due to its being incorporated into the aggregates and being released over the decomposition period of the product. In essence, this method of applying a termiticide permits it to become a slow release, long acting product. The method is also safer for workers since it eliminates the handling and potential breathing of liquids and sprays of concentrated dangerous chemicals during application.

Normally, the area to be protected will contain a building. However, in certain parts of the country, such as New Orleans, termite damage to trees is a major problem, and it is within the scope of the invention to protect trees. Preferably, the area to be protected is surrounded with the aggregates. In the case of building, it is contemplated that the aggregates will be placed near the foundation. In the case of trees, it is contemplated that the aggregates will be positioned near the base of the tree. Generally speaking, the ground around the area to be protected will be covered with the aggregates. If desired, the aggregates can be buried in the ground around the area to be protected, such as by trenching or tilling techniques. For new construction, the aggregates can be placed under the area to be occupied by the slab or foundation.

The aggregates containing the anti-termite agent are expected to function as a termite "bait"—where the termites are attracted to the product as a feed where they pick up the toxin and return to the colony to wipe it out, or as a "repellent"—where the termites either are repelled by a barrier of product or pick up toxins by contacting the product and are killed. The product is expected to be highly effective when applied as a landscape mulch in flower beds surrounding residences and other structure to be protected, such as on an annual basis. The product is expected to be highly protective when buried in the soil, forming a barrier or bait to eradicate and/or repel subterranean termites. For use as a bait, it is preferred that the aggregates contain wood products.

The anti-termite agent is incorporated into the products by spraying liquid types onto the aggregates and mixing granular types with the aggregates. Generally speaking, the aggregates will contain less than 15% by weight of the anti-termite agent, usually less than 1% but greater than 0.01%. Anti-termite agents generally include toxins and repellents. The toxin can be of the bait type. Anti-termite agents (primarily repellents) which can be incorporated into the product an exemplary wt % amount to incorporate into the aggregates include FMC Biflex TC (Bifenthrin—0.06%), FMC Talstar F (Bifenthrin—0.06%), DowElanco Dursban TC (Chlorpyrifos—0.5 to 2.0%), Whitmire Duraguard (Chlorpyrifos 1-2%), Whitmire Optem TC (Cyfluthrin 0.05-0.25%), Zeneca Demon TC (Cypermethrin 0.25%), FMC Prevail FT (Cypermethrin 0.25-1.0%), Agrevo 25 SC (Deltamethrin 0.075-0.125%), Agrevo Tribute II (Fenvalerate 0.5-1.0%), Bayer Premise 2 (Imidacloprid 0.1%), FMC F3697 (Imidacloprid 0.01-0.1%), Zeneca Karate (Lambda-cyhalothrin 0.25%), Zeneca Commodore (Lambda-cyhalothrin 0.25%), Zeneca Prelude (Torpedo) (Perethrin 0.05-1.0%), and FMC Dragnet FT (Perethrin 0.3%). Boric acid or Borax can also be used if desired. Anti termite agents (primarily "baits") which can be incorporated into the product and an exemplary wt % amount to incorporate into the aggregates include DowElanco Sentricon (Hexaflumuron 0.5%), Am Cyanamid Co. Subterfuge (Hydramethyinon 0.3%) and FMC FirstLine GT (Sulfuramid 0.01%).

In a field test, a one inch thick bed of aggregates containing either 0.1% Deltamethrin, 0.001% Deltamethrin, or no Deltamethrin were positioned on ground surface in an area known to be infested with termites and a weighted board was positioned on the top of the bed. After one year, the boards on the treated beds had been totally protected from termite attack, while the board on the untreated bed had suffered a 50% termite attack. Thus, at least for Deltamethrin, a toxin level of 0.001 wt % appears both effective and long lived.

In another aspect of this embodiment of the invention, aggregates of cellulose-containing particles which are employed as building insulation can incorporate insecticides such as those described above to prevent infestations of roaches, termites, ant, or other insects in the building. The aggregates can be in the form of a pourable crumb as is known in the art to be well suited for providing insulation above ceiling and in walls or in the form of a sprayed on insulation as is known in the art to be well suited for insulating under roofs, ceilings and floorings. The aggregates could also be blown onto the surface via an air or other gas stream or carried onto the surface via water or other liquid slurry. Because the insecticide applied in this manner will be somewhat protected from the environment; it should remain active for long periods of time, and additionally be safer for applicators than current techniques which use liquid sprays or gasses.

In another embodiment of the invention, the aggregates of cellulose particles as described above can be employed in a method for controlling fire ants. The method is carried out by selecting an area in which fire ant control is desired and applying aggregates of cellulose-containing particles containing a fire ant toxin to the area. Generally speaking, the area to be treated will be either a fire ant mound or a horticultural area. For fire ant mounds, generally from about 1 cc to about 500 cc of the aggregates will be applied, depending on the effectiveness of the toxin carried by the aggregates. For horticultural area, the aggregates will either be dispersed around the area to be protected, similar to that described above for termite control, or, more preferably, mixed with the soil. For example, fire ants can be prevented from nesting in potted plants or planters by mixing an effective amount of the aggregates containing the toxin with the soil contained in the pot or planter, or by utilizing the aggregates containing the toxin as a cover mulch for the pot or planter. The same techniques can be applied to gardens or larger agricultural areas. For lawns, the aggregates can simply be broadcast on the surface.

The toxin can be added to the aggregates in the same manner as the anti-termite agents as described above. Suitable toxins are well known in the art. Examples include Ciba Logic (Fenoxycarb), Ciba Award (Fenoxycarb), Am. Cyanamid Co. Amdro (Hydramethylnon), Ciba Diazinon granules (Diazinon), Whitmire Ascend (Abermectin), US Borax (Boric Acid), Zeneca Fireban (Tefluthrin), and FMC Talstar (Bifenthrin). The amounts of toxin are similar to that described above for the termite application.

In another embodiment of the invention, the aggregates of cellulose particles as described above can be employed in a method for controlling plant growth. The method is carried out by selecting an area in which plant growth control is desired and applying aggregates of cellulose-containing particles containing a plant growth inhibitor to the area. Generally, the type of plant growth desired to be inhibited will be weed growth or grass growth. The area to be treated will generally comprise a horticultural area. In such case, the plant growth inhibitor will generally comprise a herbicide.

It is believed that best results will be achieved in this embodiment of the invention where the horticultural area contains growing plants of the desired variety. The aggregates are applied around the growing plants so as to achieve coverage of the ground. Generally speaking, the area around the growing plants where plant growth inhibition is desired will be covered to a depth of at least 0.05 inches, generally from about 0.1 inches to about 5 inches, usually from about 0.25 to about 1 inches. The method is believed particularly well suited for application to potted plants, planters, beds and garden areas. The plant growth toxin can be added to the aggregates during the manufacturing process as hereinabove described. For such uses, it is preferred that the aggregates contain plant nutrients, and, for paper-based products, a complexing agent to slow the release of aluminum.

In this embodiment of the invention, the duration of the herbicide's effectiveness is greatly increased over current method due to its being incorporated into the aggregate and being released over the decomposition period of the aggregate. In essence, this method of applying the herbicide allows it to become a slow release herbicide. The method of incorporation and application uses less herbicides than the standard methods because none, or very little, is lost during the application to the target area. Currently 40% or more of the herbicides never effectively reach their target area due to wind, rain and water runoff. The ability of a given amount of herbicide to prevent and/or eradicate weeds is therefore increased. The method for application is also safer for workers since it eliminates the handling and potential breathing of liquids and sprays of concentrated dangerous chemicals during application. The method also eliminates the necessity of prolonged waiting periods (8 or more hours) before safe entry into an enclosed building which has recently been treated with herbicide. The training required for safe herbicide use in accordance with the invention is also lower than that currently required.

Suitable plant toxins are well known and are generally termed herbicides. They are usually incorporated into the aggregates in an amount which constitutes less than about 10 wt % of the applied material. Examples include Surflan AS (Oryzalin), Gallery 75DF (Isoxaben), Snapshot 2G (Trifluralin), Factor (Prodamine), OH-2 (Oxyfurofen+Pendimethalin), Ronstar 50 WP (Oxadiazon), Ronstar G (Oxadiazon), Ornamental weed Grass (Pendimethalin), XL 2G (Benefrin+Oryzalin), 0-0 (Oxyfurofen+Oxidiazon), Rout (Oxyfurofen+Oxidiazon), Pennant 85.1 (Metolachlor).

In another embodiment of the invention, aggregates of cellulose-containing particles are used to promote revegetation of denuded areas, such as highway right of ways. The aggregates can be generally in the form of a pourable crumb or in the form of a sprayed on covering similar to that is known in the art to be well suited for insulating under roofs, ceilings and floorings. The aggregates are employed in conjunction with a nutrient solution and vegetation seeds, such as grass seed, and preferably further contain assimilable nitrogen and other plant nutrients. This aspect of the invention is especially beneficial when applied to steeply sloped ground surfaces, such as a ground surface having a slope (run:rise) of at least 10:1, such as a slope of 4:1 or greater. The aggregates can be carried onto the surface in a stream of water or air, or mechanically applied if desired.

This aspect of the invention has been tested with good results on simulated highway right of way plots having grades of 3:1 and 2:1. A layer of cellulose containing aggregates in the form of crumbled ground paper pellets containing assimilable nitrogen and other plant nutrients was applied to the denuded ground surface of the test plots to form a bed of particles about ½ inch thick. This corresponds to an application rate of about ½ pound per square foot. The bed was then wetted with a seed/nutrient solution. The aggregates swelled and formed a mat over the test plot surface, enhancing seed germination and reducing water erosion over untreated plots and plots treated by different techniques. It is believed that the application to the ground surface of a thick slurry of seed and cellulose particles in nutrient solution would provide similar results in a more cost effective manner.

In another embodiment of the invention, seeds are adhered to an outer surface of an aggregate as hereinbefore described by use of an adhesive substance such as starch or clay. Seeds germinate poorly if simply dispersed over unturned ground and by adhering the seeds to aggregates of cellulose which are then dispersed, germination can be improved. This technique is well suited for dry broadcast techniques, for example, aerial seeding of large areas. The aggregates, preferably in pelletized or briquette form, hold moisture upon exposure to rainfall, which facilitates germination. Also, because the aggregates are resistant to being moved by wind or rain, the seeds tend to remain close to where they land and better avoid migration to and concentration in low areas.

The aggregates carrying the seeds on their outer surface are preferably further provided with a source of assimilable nitrogen, such as fertilizer, as hereinbefore described. The amount of nitrogen is greatly reduced over the amount required by large area application, since it is located precisely where needed. Initially, the seed can and will germinate and grow on the pellet. The root system eventually penetrates the earth beneath the pellet, and over time the pellet will break down and become part of the soil. Because the pellet will not easily blow or wash, the aggregates with attached seeds can be used to seed even steeply sloped areas.

The adhesive is preferably applied to the pellets by being sprayed onto the pellets in solution form, and the seeds are brought into contact with the pellets either in slurry form with the solution, or by mixing the wetted pellets with dry seeds, followed by drying under mild conditions. Adhering the seeds to the aggregate after pellet formation in this manner avoids exposure of the seeds to high pressure during the pelletizing process and to elevated temperatures during the drying process, both of which could reduce germination.

Examples of seeds which may be utilized include grass seeds such as fescue, rye, Bermuda, buffalo, bahia, blue, centipede, zoysia, blue corama, and big bluestem, grains such as wheat, oats, maize, barley and corn, and tree seeds such as pine. In arid areas, for example, the seeding could be carried out aerially, preferably, but not necessarily, shortly prior to periods of expected precipitation.

Examples of starches which may be utilized in the invention include corn starch, wheat starch, and potato starch. Clay-based adhesives such as bentonite have been tested with good results.

The amount of adhesive used can vary, but will generally be in the range of from about 1% to about 10% of the total weight of the pellet, after evaporation of the carrier fluid (generally water). The seeds are adhered to the pellets in approximately the same percentage, based on weight.

For grasses and grains, the pellets carrying the seeds are preferably applied to the soil so as to result in good ground coverage after the seeds have germinated. Generally speaking, pellets carrying bermuda, rye, or millet are applied at an application rate to result in from about 10-200 pounds of seeds per acre. Pellets carrying smaller seeds, such as bahia or native grasses, are generally applied at a rate to result in from about 1-50 pounds of seeds per acre.

In another embodiment of the invention, insect repellants are incorporated into the cellulose containing aggregates. The repellant can generally be incorporated into the pellets using the techniques generally stated herein for other additives. The repellent is preferably incorporated into the liquid used in the pelletizing process. Other additives, such as waxes and oil, can also be included in the pelletizing liquid, to provide a slower release of the repellent during conditions of use. For example, the repellent is released as the pellet breaks down during environmental conditions, mostly rainfall, encountered during use. Pellet integrity can be improved under wet conditions by incorporating wax or oil into the pellets during the pelletizing process and by the addition of binder agents, such as bentonite, into the mix used to form the pellets. Pellet integrity can also be improved by adjusting pellet size, as larger pellets are more stable.

Synthetic repellants, such as DEET (N,N-diethyl-meta-toluamide) can be used if desired. Preferably, the insect repellants are natural repellants. Examples of natural repellants include citrus oil, cedar oil, liquid garlic, cloves, citronella oil, white pepper, borax, and boric acid. More preferably, the repellant comprises an extract from a natural source. Examples of extracts include citrus oil, cedar oil, citronella oil, catnip oil, soybean oil, rosemary oil, pennyroyal oil, garlic extract, and clove extract. The amount of repellant used in the pellet is generally sufficient to provide the finished pellet with in the range of from about 0.1 to about 15 percent by weight of the repellant, preferably in the range of from about 0.5 to about 5 percent by weight of the repellant.

The pellets can be used indoors or outdoors, wherever insects are a problem. Indoors, the pellets can be used as animal bedding, or in cushions for animal bedding, to keep the bedding area free of fleas. The pellets are also effective to keep insects, especially flies and gnats, away from litter, such as cat or chicken litter, and will also counteract the odors of the litter. A residential room can be treated to repel insects, especially mosquitos, by pouring a small amount of the treated pellets into a dish, or in a pot or planter in the room, and in this application can also serve as plant mulch and as a nutrient carrier for the plants, especially when plant growth promoters have been incorporated in the pellets as taught else where herein It is expected that larger amounts of pellets are be used indoors to drive essentially all insects away, providing an alternative to fumigation, for example. Outdoors, the pellets can be used to keep an area free of mosquitos, for example, by simply broadcasting the pellets over the area In a specific example, a residential backyard can be treated to repel mosquitos for several weeks, depending on weather conditions, by broadcasting about 7 pounds (3 kilograms) of pellets containing about 2 percent by weight of cedar oil over the area. Generally speaking, it is expected that the application rate for area broadcasts of this type will be in the range of from about 10 to about 200 pounds per acre. Because the pellets break down and are assimilated beneficially into the soil over time, buildup of pellets is avoided, and since the pellets are lightweight, soft and frangible, they do not present a mowing hazard. Use of the treated pellets in planters and gardens will provide similar benefits over a wide area The pellets are also useful to repel ants from an area in which they are not desired. The pellets have a pleasant smell and raise few environment concerns, as contrasted to many insect killers presently on the market.

While certain preferred embodiments of the invention have been described herein, the invention is not to be construed as so limited, except to the extent that such limitations are found in the claims.

We claim:

1. An article of manufacture comprising
    a consolidated core consisting essentially of ground up cellulose, and
    an adhesive coating over the core carrying seeds, wherein the core is in the form of a pellet or briquette and at least 50 percent by weight of the ground up cellulose is in the form of comminuted paper particles aggregated together.

2. An article of manufacture as in claim 1 wherein the core is in the form of a pellet or briquette and the adhesive is selected the group consisting of starch and clay deposited on an outer surface of the pellet or briquette and the pellet or briquette has a circular, square, or flattened cross section.

3. An article of manufacture as in claim 2 wherein the seeds are grass seeds, said grass seeds being present in the article of manufacture in an amount in the range of from 1 to 10 weight percent, based on total weight of the article of manufacture.

4. An article of manufacture as in claim 3 which has a volume in the range of from about 0.5 to about 150 cc.

\* \* \* \* \*